United States Patent [19]

Ohtake et al.

[11] 4,269,993

[45] May 26, 1981

[54] DIARALKYLDICHLOROSILANES

[75] Inventors: Nobumasa Ohtake; Isao Koga, both of Yokohamashi; Yohji Terui, Chibashi, all of Japan

[73] Assignee: Chisso Corporation, Osaka, Japan

[21] Appl. No.: 84,574

[22] Filed: Oct. 15, 1979

[51] Int. Cl.$^3$ ............................................. C07F 7/08
[52] U.S. Cl. ...................... 556/450; 556/456; 556/479; 556/489; 556/453; 556/455
[58] Field of Search ............... 556/450, 479, 489, 456

[56] References Cited

U.S. PATENT DOCUMENTS

| | | | |
|---|---|---|---|
| 2,584,544 | 2/1952 | Bunnell | 556/489 UX |
| 2,590,039 | 3/1952 | Richter | 556/489 X |
| 2,618,646 | 11/1952 | Hatcher et al. | 556/489 UX |
| 2,759,959 | 8/1956 | Frisch | 556/479 X |
| 2,823,218 | 2/1958 | Speier et al. | 556/479 X |
| 3,546,266 | 12/1970 | Coffey | 556/479 X |
| 3,907,850 | 9/1975 | Capka et al. | 556/479 X |

Primary Examiner—Paul F. Shaver
Attorney, Agent, or Firm—Fred Philpitt

[57] ABSTRACT

Novel diaralkyldichlorosilanes expressed by the general formula (I)

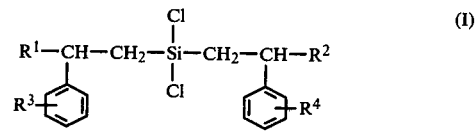

(wherein $R^1$, $R^2$, $R^3$ and $R^4$ each represent hydrogen atom or an alkyl group having 1~4 carbon atoms, but a case where $R^1$, $R^2$, $R^3$ and $R^4$ are all hydrogen atom is excluded), and a process for producing the same are provided.

They are useful as monomers for producing polysiloxanes and as intermediates for synthesizing novel organosilicon compounds.

13 Claims, 6 Drawing Figures

DIARALKYLDICHLOROSILANES

DESCRIPTION OF THE INVENTION

The present invention relates to novel organosilicon compounds, particularly to diaralkyldichlorosilanes.

Diorganodichlorosilanes among organosilicon compounds are very important compounds as bifunctional monomers for polysiloxanes. Dialkyldichlorosilanes and diphenyldichlorosilanes have heretofore been generally known, but diaralkyldichlorosilanes have never been found. Dichlorosilanes have an aralkyl group are found in U.S. Pat. No. 2,618,646, etc., but any of them are limited to those having one aralkyl group. In recent years, along with the development of silicon resin industry, organosilicon compounds which have never been found have come to be required.

The present inventors have made studies regarding the above-mentioned point and have prepared dichlorosilanes having two aralkyl groups for the first time.

The compounds of the present invention are diaralkyldichlorosilanes expressed by the general formula

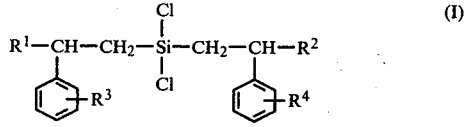

(wherein $R^1$, $R^2$, $R^3$ and $R^4$ each represent hydrogen atom or an alkyl group having 1–4 carbon atoms, but a case where $R^1$, $R^2$, $R^3$ and $R^4$ are all hydrogen atom is excluded).

Among the compounds expressed by the general formula (I), preferable ones are di-$\beta$-phenylalkyldichlorosilanes (wherein the alkyl may be the same or different, but ethyl is excluded), di-$\beta$-tolylalkyldichlorosilanes and $\beta$-phenylalkyl.$\beta$-tolylalkyldichlorisilanes, expressed by the formula (I).

As for the concrete examples of the compounds of the present invention,
di-$\beta$-phenylpropyldichlorosilane,
di-$\beta$-phenylbutyldichlorosilane,
di-$\beta$-phenylpentyldichlorosilane,
di-$\beta$-phenylhexyldichlorosilane,
di-$\beta$-tolylethyldichlorosilane,
di-$\beta$-tolylpropyldichlorosilane,
di-$\beta$-tolylbutyldichlorosilane,
di-$\beta$-tolylhexyldichlorosilane,
$\beta$-tolylethyl-$\beta$-tolylpropyldichlorosilane,
$\beta$-tolylethyl.$\beta$-tolylbutyldichlorosilane,
$\beta$-tolylpropyl.$\beta$-tolylbutyldichlorosilane,
$\beta$-phenylethyl.$\beta$-tolylethyldichlorosilane,
$\beta$-phenylethyl.$\beta$-tolylpropyldichlorosilane, etc.
can be mentioned.

The process for producing the compounds of the present invention is carried out as shown in the following equations (1) and (2):

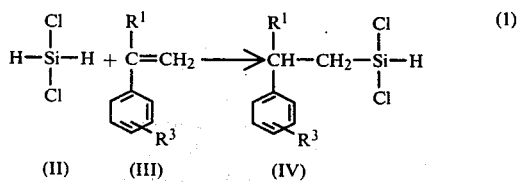

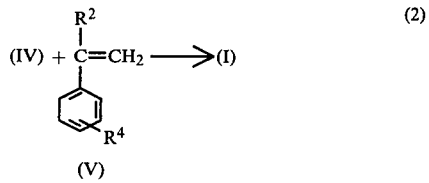

(Wherein $R^1$, $R^2$, $R^3$ and $R^4$, each represent hydrogen atom or an alkyl group, but a case where $R^1$, $R^2$, $R^3$ and $R^4$ are all hydrogen atom is excluded).

Firstly, dichlorosilane (II) is subjected to addition reaction with styrene or a styrene derivative (III) at a temperature of 30°–200° C. in the presence of a complex catalyst of a transition metal of VIII group of the Periodic Table and a phosphine compound, to form a monoaralkyldichlorosilane (IV), as shown in the above equation (1).

Next, this monoaralkyldichlorosilane (IV) is subjected to addition reaction with styrene or a styrene derivative (V) at a temperature of 10°–200° C. in the presence of a complex catalyst of a transition metal of VIII group of the Periodic Table and a phosphine compound or in the presence of chloroplatinic acid (but, in case where $R^2$ is hydrogen atom in the equation (2), chloroplatinic acid is not employed), to form a diaralkyldichlorosilane (I), as shown in the equation (2).

As for the concrete examples of the styrene derivative, $\alpha$-methylstyrene, $\alpha$-ethylstyrene, $\alpha$-propylstyrene, $\alpha$-butylstyrene, methylstyrene(vinyltoluene), $\alpha$-methyl-methylstyrene, $\alpha$-ethyl-methylstyrene, $\alpha$-propyl-methylstyrene, $\alpha$-butyl-methylstyrene, etc. are mentioned. As for the methylstyrene and methylstyrene derivatives, ortho-, metha- and para-compounds and the mixtures thereof are mentioned.

Said complex of a transition metal of VIII group of the Periodic Table and a phosphine compound is preferably a complex represented by the general formula of $MX_n(PR_3°)_m$ wherein $R°$ is phenyl (hereinafter abbreviated to Ph), aryl, alkyl or aralkyl; M is a metal selected from ruthenium, rhodium, nickel and platinum; X is a covalently bound halogen or hydrogen atom, a covalently bound substituted silyl group, or a non-covalently bound carbon monoxide molecule or aromatic hydrocarbon compound; and n is an interger of 0 to 4 and m is an integer of 2 to 4 provided that $3 \leq (n+m) \leq 7$. For example, as the transition metal-phosphine compound complex, such as $RhH(PPh_3)_4$, $RhH(CO)(PPh_3)_3$, $RhCl(CO)(PPh_3)_2$, $RhCl(PPh_3)_3$, $RuCl_2(PPh_3)_3$, $RuHCl(PPh_3)_3[C_6H_6]$, $RuHCl(PPh_3)_3[C_6H_5CH_3]$, $RuH_3(PPh_3)_3[Si(OCH_3)_3]$, $RuH_3(PPh_3)_3.[Si(OCH_3)_2PH]$, $RuH(PPh_3)_3[Si(C_2H_5)_2Cl]$, $RuH_2(PPh_3)_4$, $NiCl_2(PPh_3)_2$ and $Pt(PPh_3)_4$ can be mentioned.

Particularly when styrene or styrene derivatives having no substituent at $\alpha$-position are employed, $Pt(PPh_3)_4$ is preferable.

Diaralkyldichlorosilanes of the present invention, when heated with water, form silanols and/or cyclic siloxanes, which, in turn, when heated in the presence of an acid or a base as a catalyst, are polycondensed to form polymers. Further, it is also possible to hydrolyze at least one of diaralkyldichlorosilanes of the present invention together with at least one of other organodichlorosilanes and then copolycondense the resulting silanols and/or cyclic siloxanes.

The diaralkyldichlorosilanes of the present invention are novel compounds and useful as monomers for polysiloxanes for improving properties of silicone oils and varnishes employed for electrical insulating materials, lubricating oils, water repellents, paints and lacquers, release agents, etc. Further, it is possible to utilize them as intermediates for synthesizing novel organosilicon compounds.

EXAMPLE 1

α-Methylstyrene (154 g) (1.3 mol) and chlorotris(triphenylphosphine)rhodium [RhCl(PPh$_3$)$_3$] (0.9 g) (1.0×10$^{-3}$ mol) were introduced into a 500 ml stainless steel pressure reactor, which was then closed. The reactor was cooled in a dry ice-methanol bath, and dichlorosilane (101 g) (1.0 mol) was introduced therein through an introducing tube, followed by sealing. Reaction was carried out with stirring at 70° C. for 7 hours. The resulting reaction liquid was distilled in vacuo to obtain 192 g of a product having a boiling point of 103° C./9.5 mmHg. Its I.R. spectra showed an absorption specific of Si—H at 2,205 cm$^{-1}$, and the δ value (ppm) of its NMR spectra showed signals by proton, of Si—H, —CH$_2$—Si,

and CH$_3$C$_6$H$_5$ at 5.28, 1.54, 3.13, 1.35 and 7.19, respectively. Thus it was confirmed that the product was mono-β-phenylpropyldichlorosilane [CH$_3$CH(C$_6$H$_5$)CH$_2$SiHCl$_2$].

Figure 1:
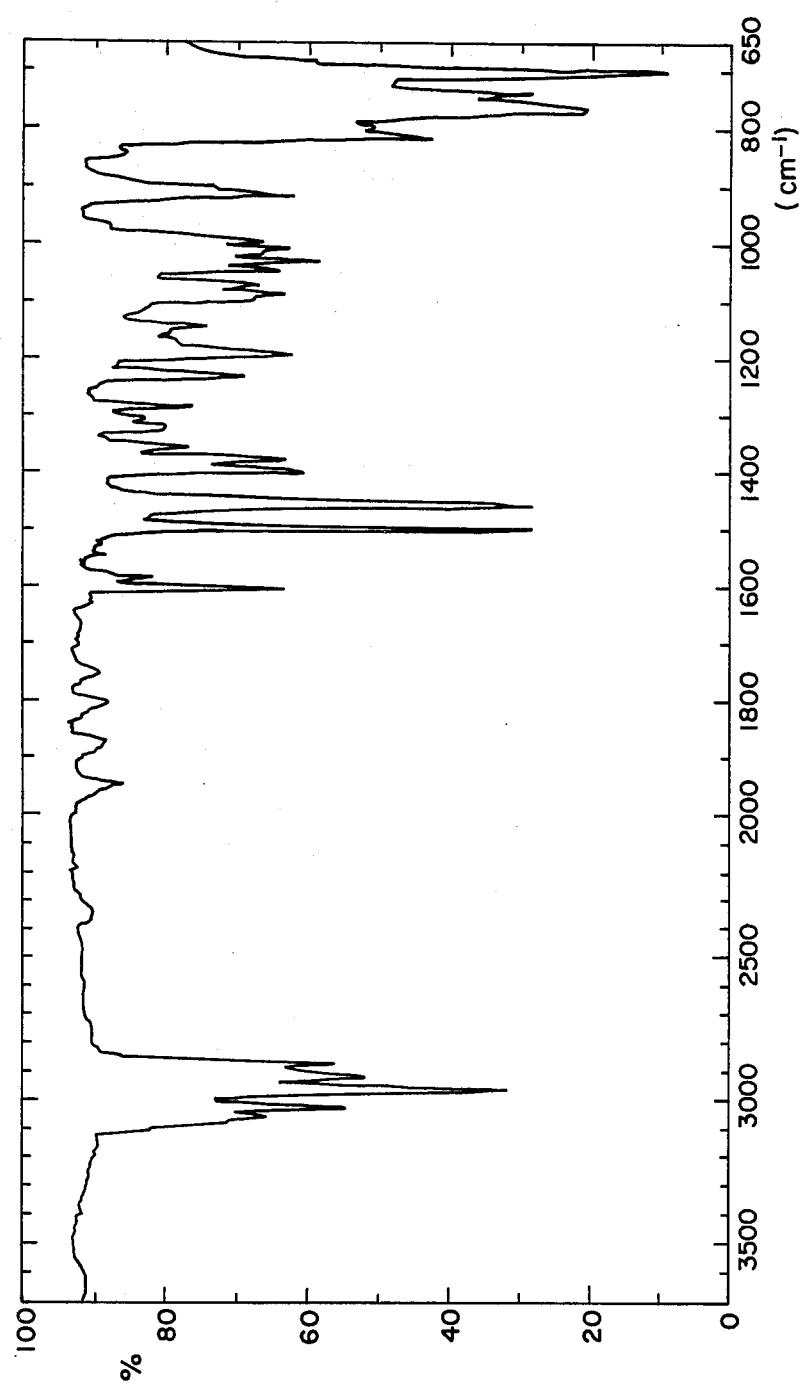
FIG. 1 shows the infrared ray absorption spectra (abbreviated to I.R.) of di-β-phenylpropyldichlorosilane.
Figure 2:
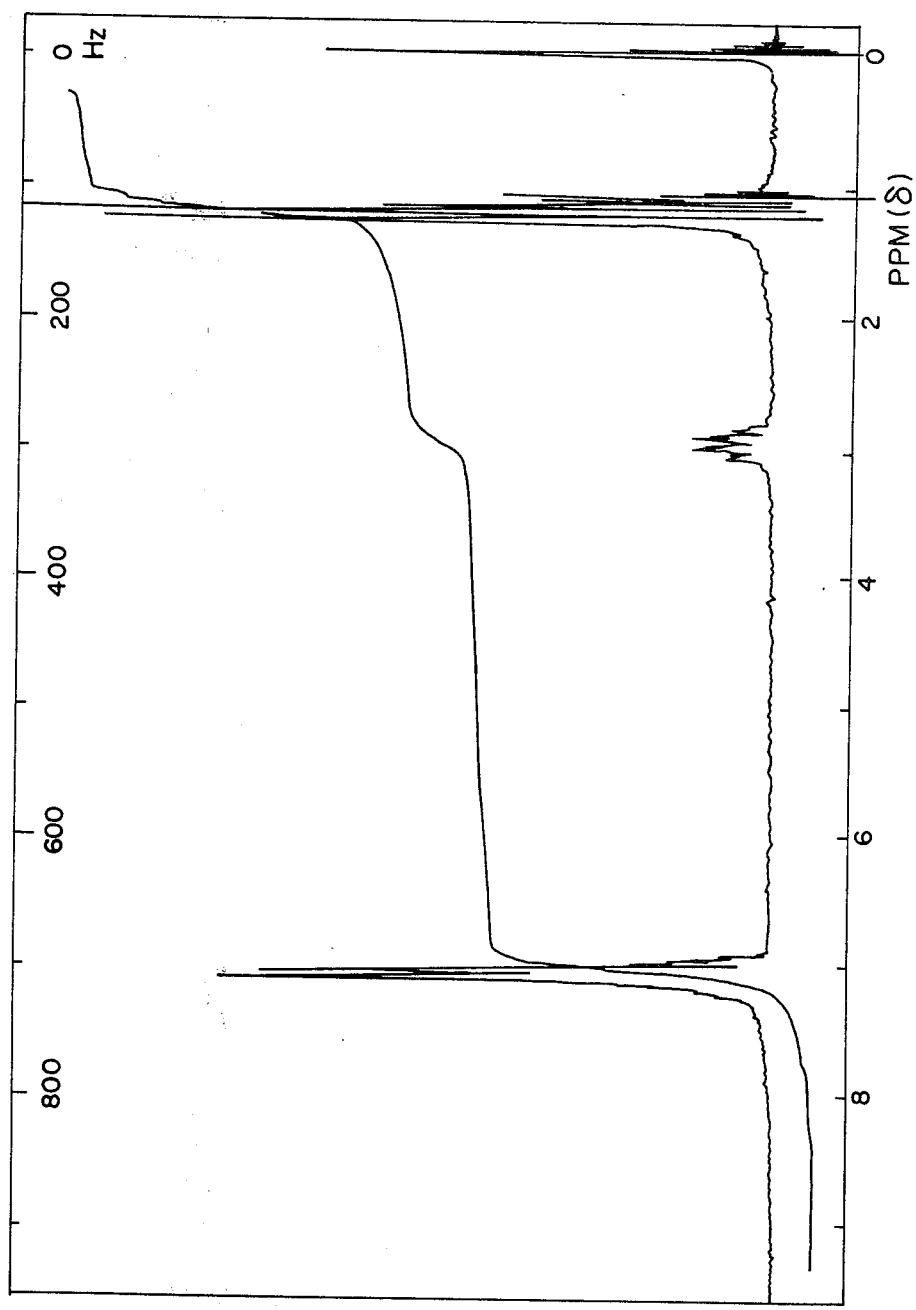
FIG. 2 shows its nuclear magnetic resonance spectra (NMR).

This β-phenylpropyldichlorosilane (66 g) (0.3 mol), chloroplatinic acid (0.031 g) (6×10$^{-5}$ mol) and α-methylstyrene (71 g) (0.6 mol) were fed into a flask to carry out reaction at 20°–30° C. for 5 hours. The reaction liquid was distilled in vacuo to obtain 85 g of a product having a boiling point of 160°–161° C./2.5 mmHg. This product had a n$_D^{20}$ of 1.5446, and its I.R. is shown in FIG. 1 and its NMR is shown in FIG. 2. Thus it was confirmed that this product was di-β-phenylpropyldichlorosilane [(C$_6$H$_5$.CH.CH$_3$CH$_2$)$_2$SiCl$_2$].

EXAMPLE 2

Figure 3:
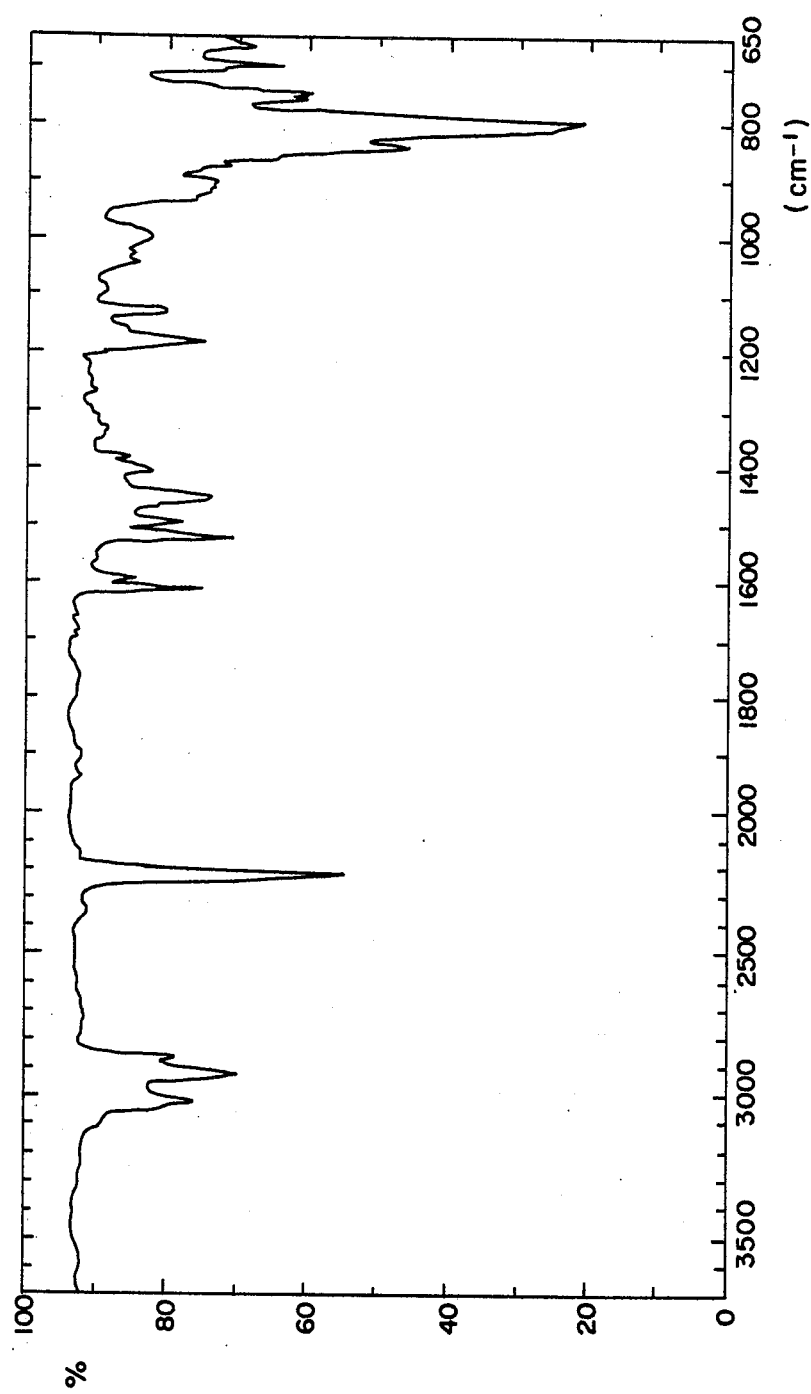
FIG. 3 shows I.R. of mono-β-tolylethyldichlorosilane.
Figure 4:
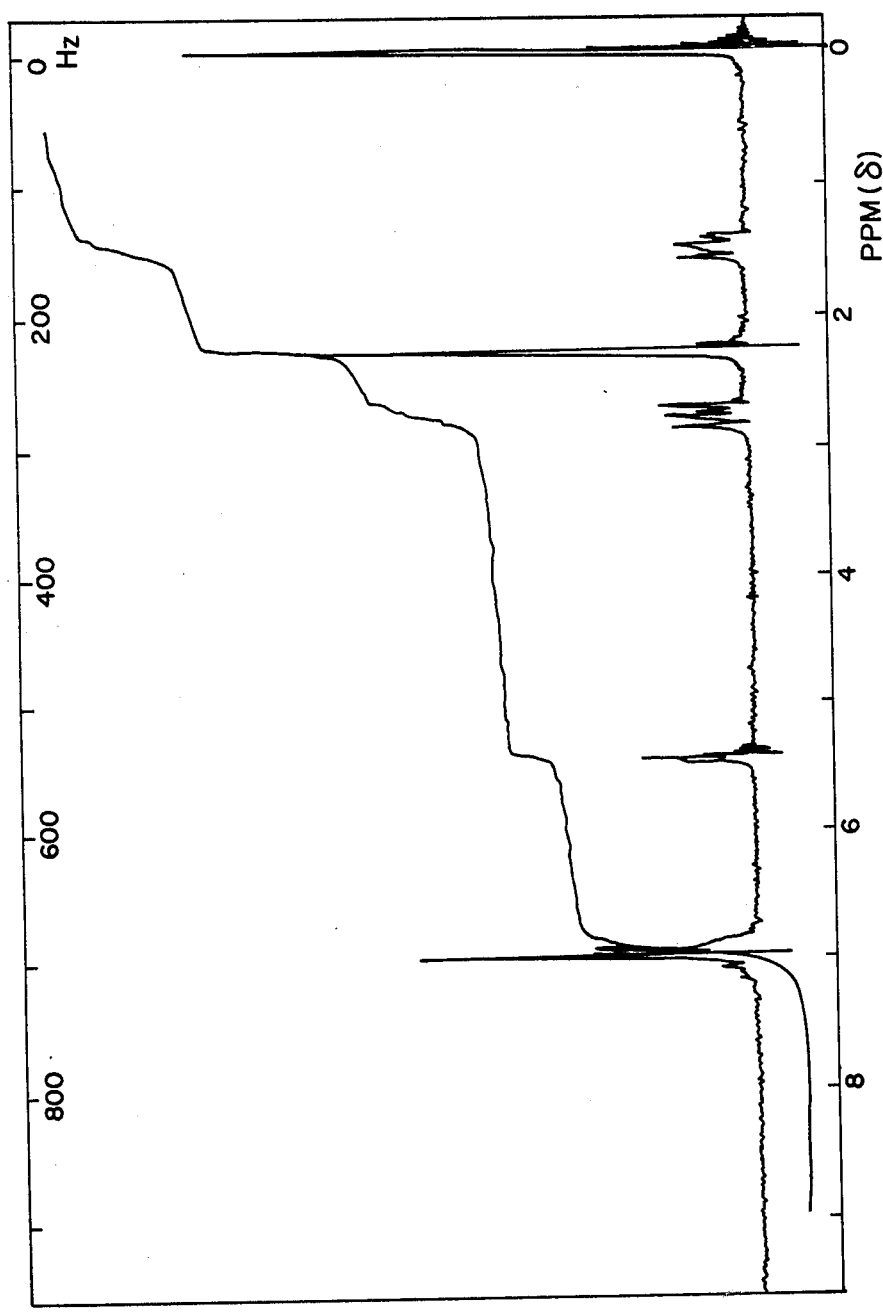
FIG. 4 shows its NMR.

Vinyltoluene [metha-form (m): para-form (p)=65:35 (molar ratio] (154 g) (1.3 mol) and chlorotris(triphenylphosphine)rhodium [RhCl(PPh$_3$)] (0.9 g) (1.0×10$^{-3}$ mol) were introduced into a 500 ml stainless steel pressure reactor, which was then closed. The reactor was cooled in a dry ice-methanol bath, and dichlorosilane (101 g) (1.0 mol) was introduced therein through an introducing tube, followed by sealed. Reaction was carried out at 70° C. for 8 hours. The resulting reaction liquid was distilled in vacuo to obtain 196.7 g of a product having a boiling point of 110° C./10 mmHg. This product had an I.R. shown in FIG. 3 and a NMR shown in FIG. 4. Thus it was confirmed that the product was mono-β-tolylethyldichlorosilane (a mixture of m-form with p-form).

Figure 5:
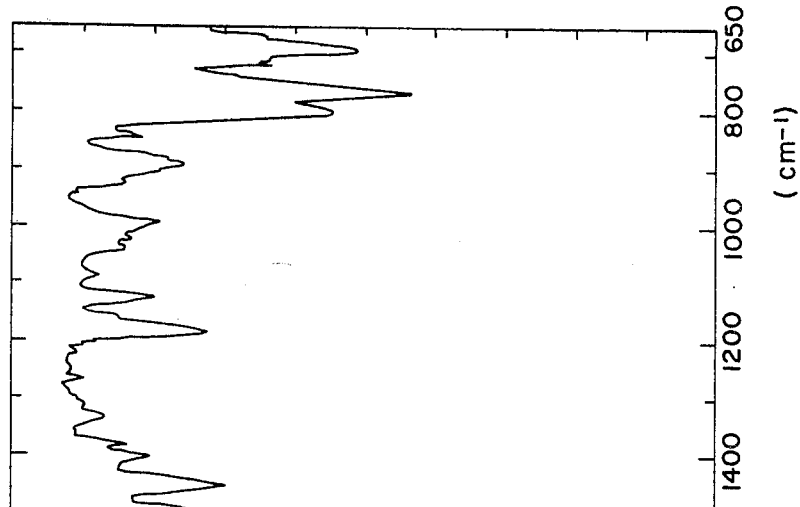
FIG. 5 shows I.R. of di-β-tolylethyldichlorosilane
Figure 6:
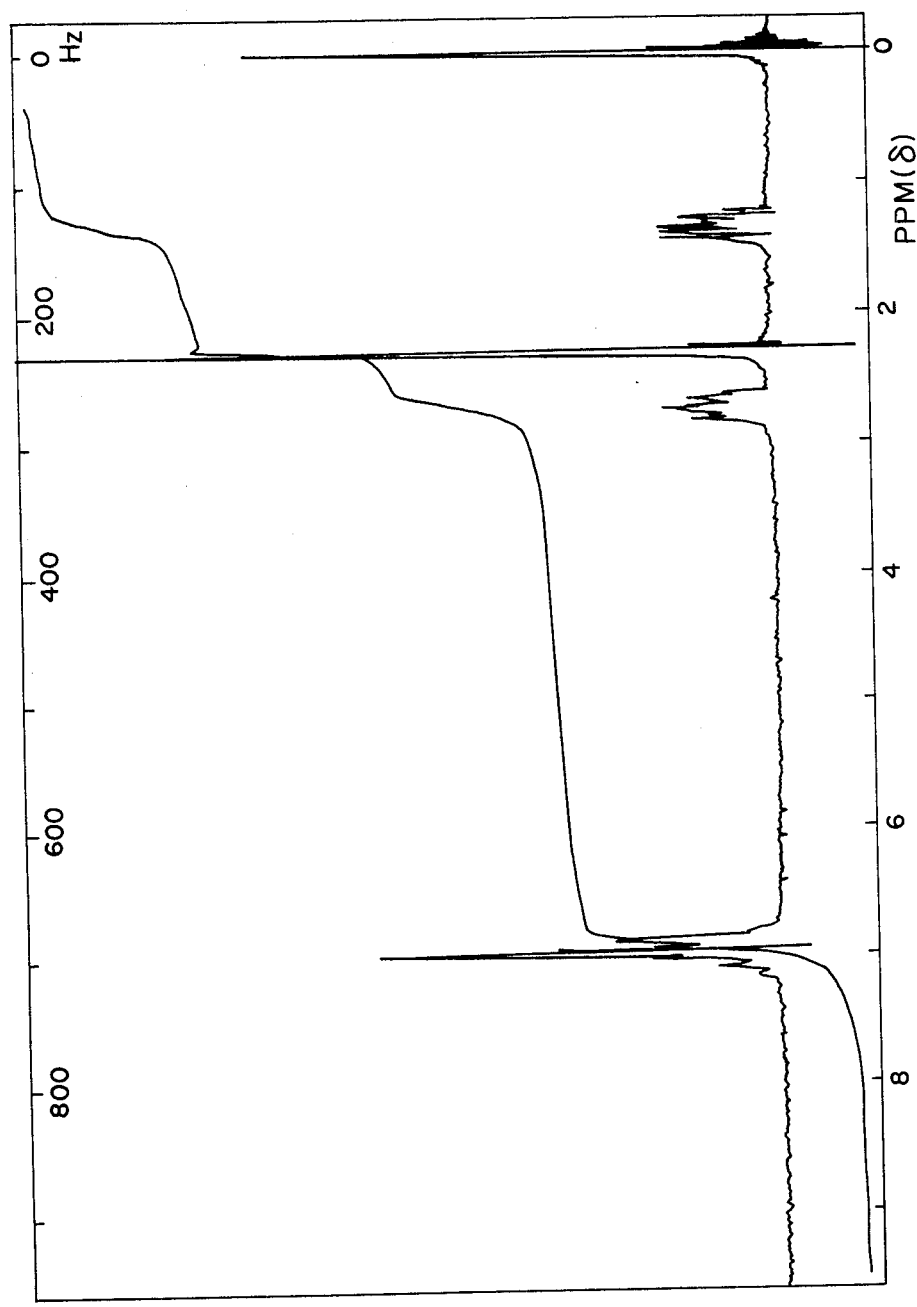
FIG. 6 shows its NMR.

This β-tolylethyldichlorosilane (109.5 g) (0.5 mol), tetrakis(triphenylphosphine)platinum(O) [Pt(PPh$_3$)$_4$] (0.62 g) (5×10$^{-4}$ mol) and vinyltoluene (m:p (molar ratio)=65:35) (118 g) (1.0 mol) were fed into a 500 ml flask, and reaction was carried out under nitrogen atmosphere at 100° C. for 8 hours. The resulting reaction liquid was distilled to obtain 153.7 g of a product having a boiling point of 186°–187° C./3 mmHg. This product had a n$_D^{20}$ of 1.5463 and exhibited an I.R. shown in FIG. 5 and a NMR shown in FIG. 6. Thus it was confirmed that this product was di-β-tolylethyldichlorosilane [(CH$_3$C$_6$H$_4$CH$_2$CH$_2$)$_2$SiCl$_2$].

EXAMPLE 3

Dichlorosilane (31.7 g) (314 millimols), styrene (56.3 g) (541 millimols) and chlorotris(triphenylphosphine)rhodium (0.2182 g) (2.36×10$^{-4}$ mol) were nitroduced into a 200 ml stainless steel reactor, which was then closed. Reaction was carried out with stirring on heating in an oil bath at 150° C. for 20 hours. The resulting reaction liquid was distilled in vacuo to obtain 45.7 g of mono-β-phenylethyldichlorosilane.

This mono-β-phenylethyldichlorosilane (41 g) (0.2 mol), chloroplatinic acid (0.02 g) (4×10$^{-5}$ mol) and α-methylstyrene (47.3 g) (0.4 mol) were fed into a flask to carry out reaction at 20°–30° C. for 5 hours to obtain β-phenylethyl.β-phenylpropyldichlorosilane.

EXAMPLE 4

Mono-β-phenylpropyldichlorosilane obtained in Example 1 (66 g) (0.3 mol), styrene (104 g) (1.0 mol) and tetrakis(triphenylphosphine)platinum (0) (0.08 g) (6.42×10$^{-5}$ mol) were introduced into a 300 ml stainless steel reactor, and reaction was carried out with stirring on heating in an oil bath at 100° C. for 15 hours to obtain β-phenylethyl.β-phenylpropyldichlorosilane.

COMPARATIVE EXAMPLE 1

Dichlorosilane (30.0 g) (0.3 mol), styrene (56.5 g) (0.543 mol) and an isopropanol solution (50 ml) of chloroplatinic acid [H$_2$PtCl$_6$.6H$_2$O, 4.83×10$^{-6}$ mol] were introduced into a 200 ml stainless steel reactor. Reaction was carried out with stirring on heating in an oil bath at 50° C. for 15 hours. The resulting reaction liquid resinified.

EXAMPLE 5

Di-β-phenylpropyldichlorosilane (145 g) obtained in Example 1 was dropwise added with stirring to 200 g of a water-diisopropyl ether mixture (water 165 g and diisopropyl ether 40 g) maintained at 60° C., over one hour, and after the addition, reaction was carried out with stirring for 4 hours. The aqueous phase portion of the resulting reaction liquid was removed, and the ether solution of the resulting product was washed five times with 50 ml of water. After it was confirmed that the washed water became alkaline, 50 ml of toluene was added to the ether solution, and toluene, ether and water were removed by vaporization at 100° C. in vacuo to obtain 105 g of a product.

To this product (96 g) were added 3.0 g of hexamethyldisiloxane, and further, with stirring, 1 ml of a 10% aqueous solution of tetramethylammonium hydroxide [(CH$_3$)$_4$NOH] and 10 ml of toluene, and the mixture was heated up to 80° C. The water of the 10% aqueous solution was distilled off by blowing nitrogen gas into the reaction liquid, followed by reaction with stirring at 80° C. for 10 hours. After the reaction, 75 ml of toluene was added to obtain a toluene solution, which was then washed three times with 80 ml of water. After the solution became neutral, toluene was distilled off at 100° C. to obtain 93.0 g of a polysiloxane.

What is claimed is:

1. Di-β-phenylalkyldichlorosilanes expressed by the general formula

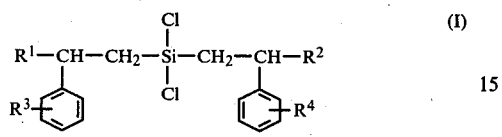

wherein $R^1$ and $R^2$ each represent an alkyl group of 1 to 4 carbon atoms or one of them represents hydrogen atom and the other represents an alkyl group of 1 to 4 carbon atoms, and $R^3$ and $R^4$ each represent hydrogen atom.

2. Di-β-phenylpropyldichlorosilane.

3. Di-β-phenylethyldichlorosilane.

4. Di-β-tolylalkyldichlorosilane expressed by the general formula

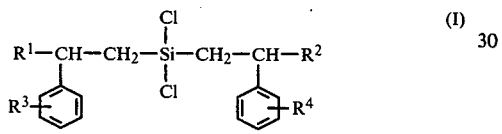

wherein $R^1$ and $R^2$ each represent a hydrogen atom or an alkyl group of 1 to 4 carbon atoms and $R^3$ and $R^4$ each represent a methyl group.

5. Di-β-tolylethyldichlorosilanes.

6. β-phenylalkyl-β-tolylalkyl-dichlorosilanes expressed by the general formula

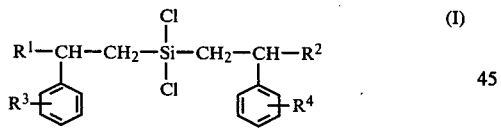

wherein $R^1$ and $R^2$ each represent a hydrogen atom or an alkyl group of 1 to 4 carbon atoms, and one of $R^3$ and $R^4$ represents a methyl group and the other represents hydrogen atom.

7. Compounds of claim 1, obtained by reacting diclorosilanes with styrene at a temperature of 30° to 200° C. in the presence of a complex expressed by the general formula $MX_n(PR_3°)_m$ wherein $R°$ is phenyl, aryl, alkyl or aralkyl; M is a metal selected from ruthenium, rhodium, nickel, and platinum; X is a covalently bound halogen or hydrogen atom, a covalently bound substituted silyl group, or a non-covalently bound carbon monoxide molecule or aromatic hydrocarbon compounds; and n is an integer of 0 to 4 and m is an integer of 2 to 4 provided that $3 \leq (n+m) \leq 7$ (which complex will be hereinafter referred to as complex $MX_n(PR_3°)_m$) to form a β-phenylethyldichlorosilane; and reacting this β-phenylethyldicholorsilane with an α-alkylstyrene selected from the group consisting of α-methylstyrene, α-ethylstyrene, α-propylstyrene and α-butylstyrene, at a temperature of 10° to 200° C. in the presence of said complex $MX_n(PR_3°)_m$ or chloroplatinic acid.

8. Compounds of claim 1, obtained by reacting dichlorosilane with an α-alkylstyrene selected from the group consisting of α-methylstyrene, α-ethylstyrene, α-propylstyrene and α-butylstyrene at a temperature of 30° to 200° C. in the presence of a complex expressed by the general formula $MX_n(PR_3°)_m$ wherein $R°$ is a phenyl, aryl, alkyl or aralkyl; M is a metal selected from ruthenium, rhodium, nickel, and platinum; X is a covalently bound halogen or hydrogen atom, a covalently bound substituted silyl group, or a non-covalently bound carbon monoxide molecule or aromatic hydrocarbon compound; and n is an integer of 0 to 4 and m is an integer of 2 to 4 provided that $3 \leq (n+m) \leq 7$, to form a β-phenylalkyldichlorosilane; and reacting this β-phenylalkyldichlorosilane with styrene at a temperature of 10° to 200° C. in the presence of said complex.

9. Compounds of claim 4, obtained by reacting dichlorosilane with a methylstyrene selected from the group consisting of ortho-, meta-, and para-methylstyrenes and a mixture thereof, or a methylstyrene derivative of ortho-, meta- or paraform selected from the group consisting of α-methyl-methylstyrene, α-ethyl-methylstyrene, α-propyl-methylstyrene and α-butyl-methylstyrene and a mixture thereof, at a temperature of 30° to 200° C. in the presence of a complex expressed by the general formula $MX_n(PR_3°)_m$ wherein $R°$ is a phenyl, aryl, alkyl or aralkyl; M is a metal selected from ruthenium, rhodium, nickel, and platinum; X is a covalently bound halogen or hydrogen atom, a covalently bound substituted silyl group, or a non-covalently bound carbon monoxide molecule or aromatic hydrocarbon compound; and n is an integer of 0 to 4 and m is an integer of 2 to 4 provided that $3 \leq (n+m) \leq 7$, to form a p-tolylalkyldichlorosilane; and reacting this p-tolylalkyldichlorosilane with said methylstyrene in the presence of said complex, or with said methylstyrene derivative in the presence of said complex or chloroplatinic acid, at a temperature of 10° to 200° C.

10. Compounds of claim 6, obtained by reacting dichlorosilane with a styrene compound selected from the group consisting of styrene, α-methylstyrene, α-ethylstyrene, α-propylstyrene and α-butylstyrene at a temperature of 30° to 200° C. in the presence of a complex expressed by the general formula $MX_n(PR_3°)_m$ wherein R° is phenyl, aryl, alkyl or aralkyl; M is a metal selected from ruthenium, rhodium, nickel, and platinum; X is a covalently bound halogen or hydrogen atom, a covalently bound substituted silyl group, or a non-covalently bound carbon monoxide molecule or aromatic hydrocarbon compound; and n is and integer of 0 to 4 and m is an integer of 2 to 4 provided that $3 \leq (n+m) \leq 7$, to form a β-phenylalkyldichlorosilane; and reacting this β-phenylalkyldichlorosilane with a methylstyrene selected from the group consisting of ortho-, meta- and para-methylstyrenes and a mixture thereof, in the presence of said complex or with a methylstyrene derivative of ortho-, meta- or para-form selected from the group consisting of α-dimethylstyrene, α-ethyl-methylstyrene, α-propyl-methylstyrene and α-butyl-methylstyrene and a mixture thereof, in the presence of said complex or chloroplatinic acid, at a temperature of 10° to 200° C.

11. Compounds of claim 6, obtained by reacting dichlorosilane with a methylstyrene selected from the group consisting of ortho-, meta- and para-methylstyrenes and a mixture thereof, or a methylstyrene derivative of ortho-, meta- or para-form selected from the group consisting of α-dimethylstyrene, α-ethyl-methylstyrene, α-propyl-methylstyrene and α-butyl-methylstyrene and a mixture thereof, at a temperature of 30° to 200° C.

in the presence of a complex expressed by the general formula

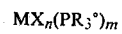

wherein R° is phenyl, aryl, alkyl, or aralkyl; M is a metal selected from ruthenium, rhodium, nickel, and platinum; X is a covalently bound halogen or hydrogen atom, a covalently bound substituted silyl group, or a non-covalently bound carbon monoxide molecule or aromatic hydrocarbon compound; and n is an integer of 0 to 4 and m is an integer of 2 to 4 provided that $3 \leq (n+m) \leq 7$, to form a p-tolyl alkyldichlorosilane; and reacting this p-tolylalkyldichlorosilane with styrene in the presence of said complex, or with an α-alkylstyrene selected from the group consisting of α-methylstyrene, α-ethylstyrene, α-propylstyrene and α-butylstyrene in the presence of said complex or chloroplatinic acid, at a temperature of 10° to 200° C.

12. Polysiloxanes obtained by hydrolyzing a di-β-tolylalkyldichlorosilane and then subjecting the resulting hydrolyzate to poylcondensation.

13. Polysiloxanes according to claim 12 wherein said di-β-tolylalkyldichlorosilane is di-β-tolylethyldichlorosilane.

* * * * *